United States Patent
Jones et al.

(10) Patent No.: US 8,366,714 B2
(45) Date of Patent: Feb. 5, 2013

(54) ROD INSERTION INSTRUMENT AND METHOD OF USE

(75) Inventors: Scott Jones, McMurray, PA (US); Catherine Ross, Stafford, VA (US)

(73) Assignee: K2M, Inc., Leesburg, VA (US)

( * ) Notice: Subject to any disclaimer, the term of this patent is extended or adjusted under 35 U.S.C. 154(b) by 822 days.

(21) Appl. No.: 12/256,948

(22) Filed: Oct. 23, 2008

(65) Prior Publication Data
US 2009/0105774 A1 Apr. 23, 2009

Related U.S. Application Data

(60) Provisional application No. 60/999,946, filed on Oct. 23, 2007.

(51) Int. Cl.
*A61B 17/70* (2006.01)
(52) U.S. Cl. .......... 606/86 A; 606/99; 606/104; 606/914
(58) Field of Classification Search ............. 279/52, 279/53, 42, 43; 606/99, 914–916, 86 A, 606/103, 104, 250–279, 86 B; 81/177.75, 81/177.6, 177.7
See application file for complete search history.

(56) References Cited

U.S. PATENT DOCUMENTS

| | | | | |
|---|---|---|---|---|
| 797,684 | A * | 8/1905 | Harper | 433/147 |
| 3,549,159 | A * | 12/1970 | Kroener | 279/53 |
| 3,752,202 | A * | 8/1973 | Condon | 81/436 |
| 3,940,946 | A * | 3/1976 | Andersen | 464/89 |
| 5,069,569 | A * | 12/1991 | Lieser | 403/57 |
| 5,213,015 | A * | 5/1993 | Disston, Jr. | 81/90.9 |
| 5,364,397 | A | 11/1994 | Hayes et al. | |
| 5,443,464 | A * | 8/1995 | Russell et al. | 606/54 |
| 5,707,371 | A | 1/1998 | Metz-Stavenhagen | |
| 5,720,751 | A | 2/1998 | Jackson | |
| 5,738,586 | A * | 4/1998 | Arriaga | 464/106 |
| 5,910,141 | A | 6/1999 | Morrison et al. | |
| 6,319,257 | B1 * | 11/2001 | Carignan et al. | 606/99 |
| 6,660,006 | B2 | 12/2003 | Markworth et al. | |
| 6,860,889 | B2 * | 3/2005 | Bonati et al. | 606/104 |
| 7,226,453 | B2 | 6/2007 | Chao et al. | |
| 7,335,207 | B1 * | 2/2008 | Smith | 606/99 |
| 7,371,239 | B2 | 5/2008 | Dec et al. | |
| 7,491,207 | B2 | 2/2009 | Keyer et al. | |
| 7,682,363 | B2 * | 3/2010 | Burgi et al. | 606/91 |
| 7,922,731 | B2 * | 4/2011 | Schumacher et al. | 606/104 |
| 7,966,915 | B2 * | 6/2011 | Chen | 81/177.75 |
| 7,998,144 | B2 * | 8/2011 | Schumacher et al. | 606/99 |
| 2003/0050645 | A1 * | 3/2003 | Parker et al. | 606/99 |
| 2004/0147937 | A1 | 7/2004 | Dunbar et al. | |

(Continued)

FOREIGN PATENT DOCUMENTS

| | | |
|---|---|---|
| WO | WO 01/97677 | 12/2001 |
| WO | WO 02/091932 | 11/2002 |

(Continued)

*Primary Examiner* — Jan Christopher Merene
(74) *Attorney, Agent, or Firm* — Carter, DeLuca, Farrell & Schmidt, LLP

(57) ABSTRACT

An insertion tool for inserting a spinal rod into a patient is provided. The insertion tool includes an upper body portion defining a first longitudinal axis, a handle assembly extending from the upper body portion, an elbow member connected to a distal end of the body portion, a lower body portion defining a second longitudinal axis, and a drive mechanism extending between the handle assembly and the lower body portion for controlling the selective engagement of the spinal rod. The lower body portion extends from the elbow and is configured to selectively engage a spinal rod.

17 Claims, 18 Drawing Sheets

U.S. PATENT DOCUMENTS

| | | | | |
|---|---|---|---|---|
| 2004/0158257 | A1* | 8/2004 | Bonati et al. | 606/99 |
| 2004/0215190 | A1* | 10/2004 | Nguyen et al. | 606/61 |
| 2004/0267275 | A1 | 12/2004 | Cournoyer et al. | |
| 2005/0038443 | A1* | 2/2005 | Hedley et al. | 606/91 |
| 2006/0079894 | A1* | 4/2006 | Colleran et al. | 606/61 |
| 2007/0123867 | A1* | 5/2007 | Kirschman | 606/61 |
| 2007/0213714 | A1* | 9/2007 | Justis | 606/61 |
| 2007/0293869 | A1* | 12/2007 | Conte et al. | 606/91 |
| 2008/0077136 | A1 | 3/2008 | Triplett et al. | |
| 2008/0154280 | A1* | 6/2008 | Schumacher et al. | 606/104 |
| 2008/0177318 | A1* | 7/2008 | Veldman et al. | 606/256 |

FOREIGN PATENT DOCUMENTS

WO    WO 03/034925    5/2003

\* cited by examiner

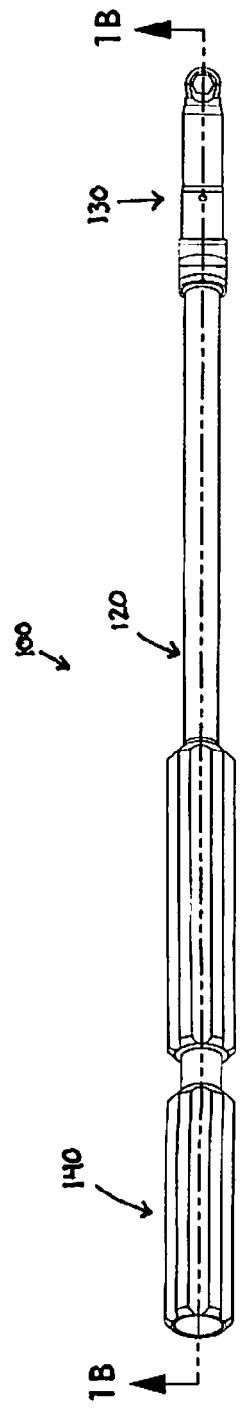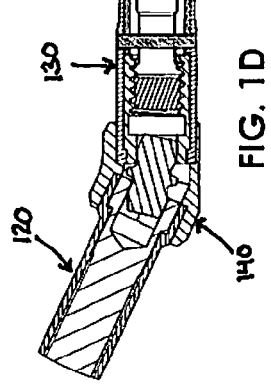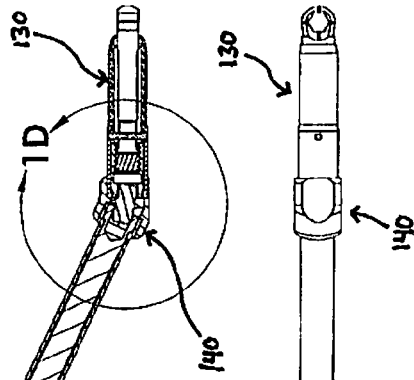

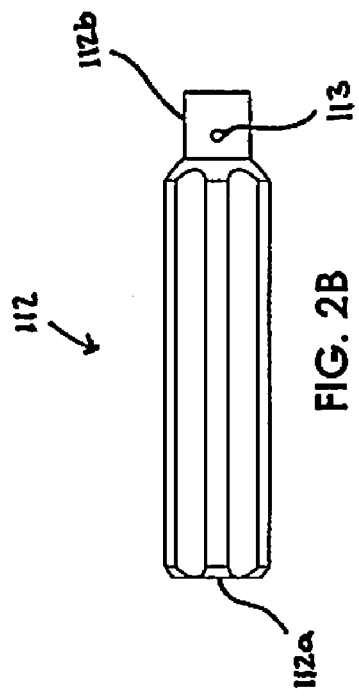
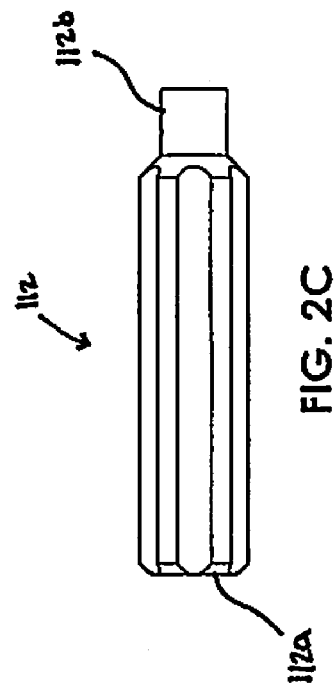
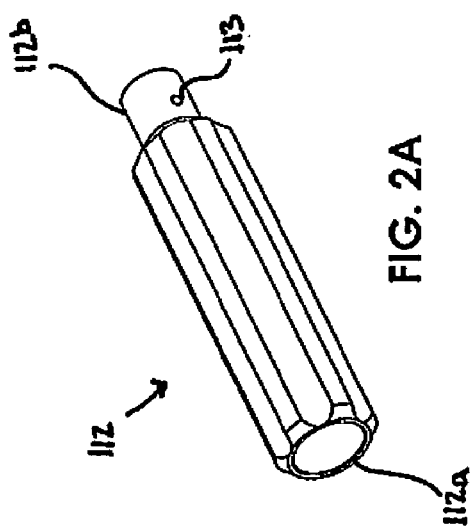

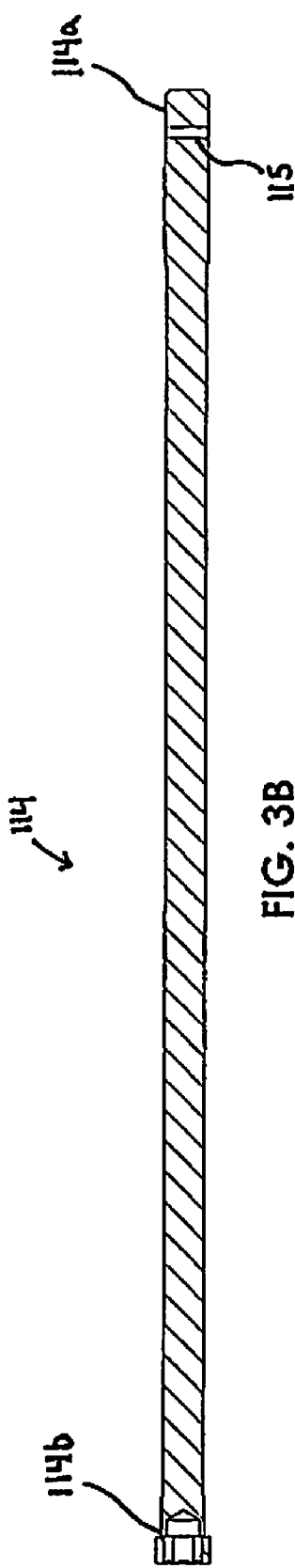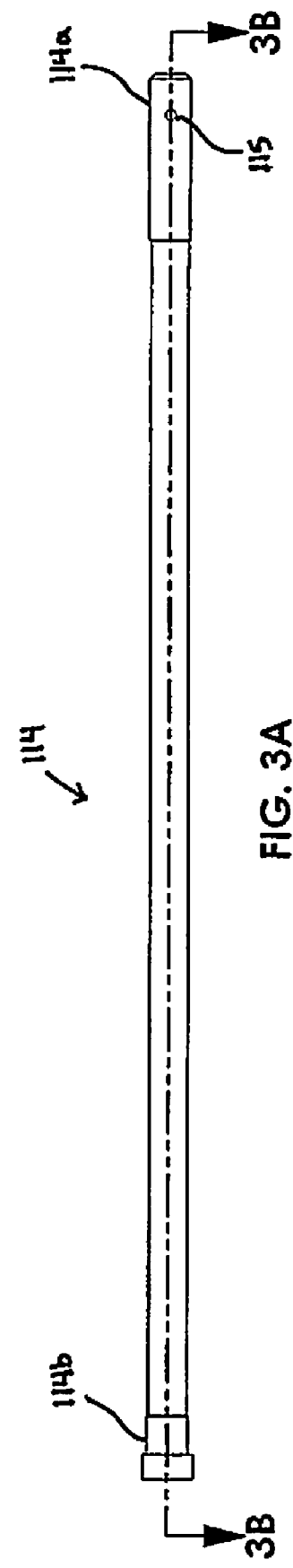
FIG. 3A
FIG. 3B

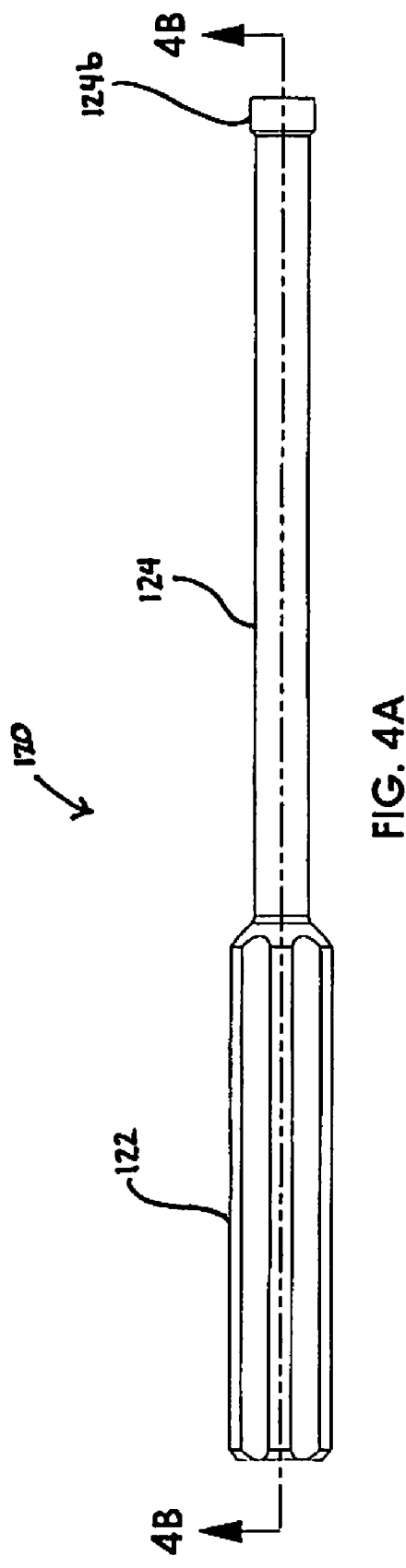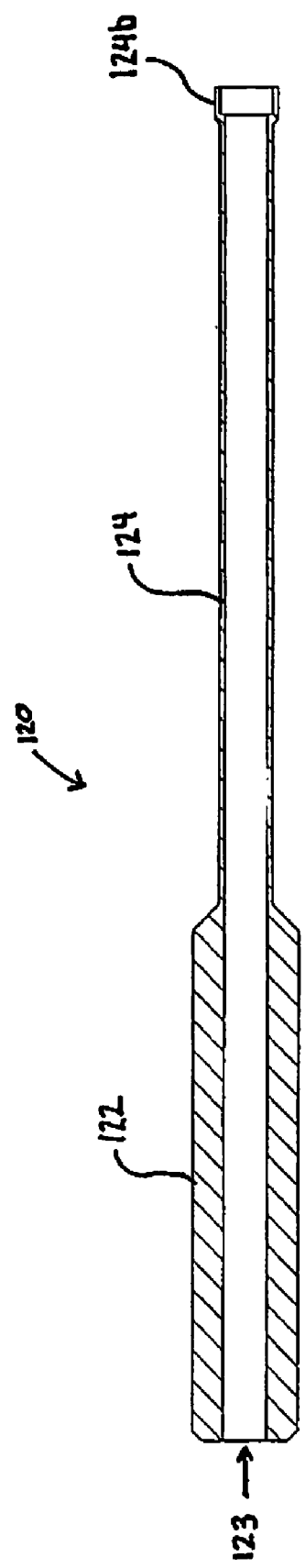
FIG. 4A
FIG. 4B

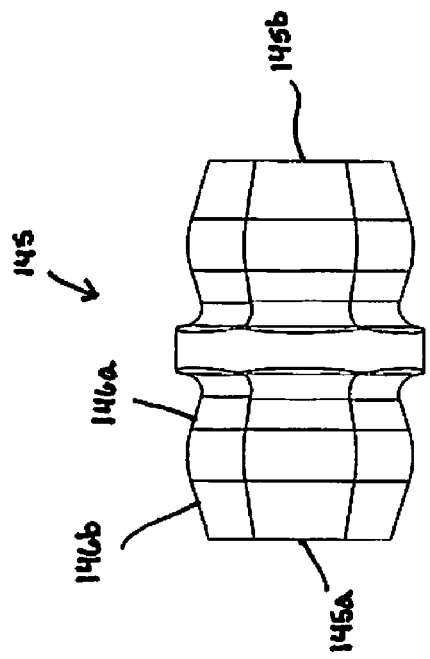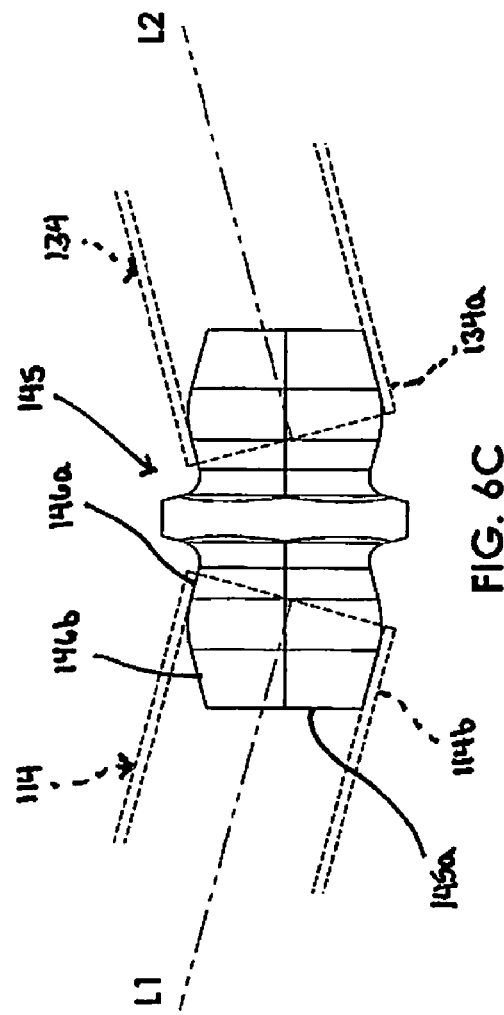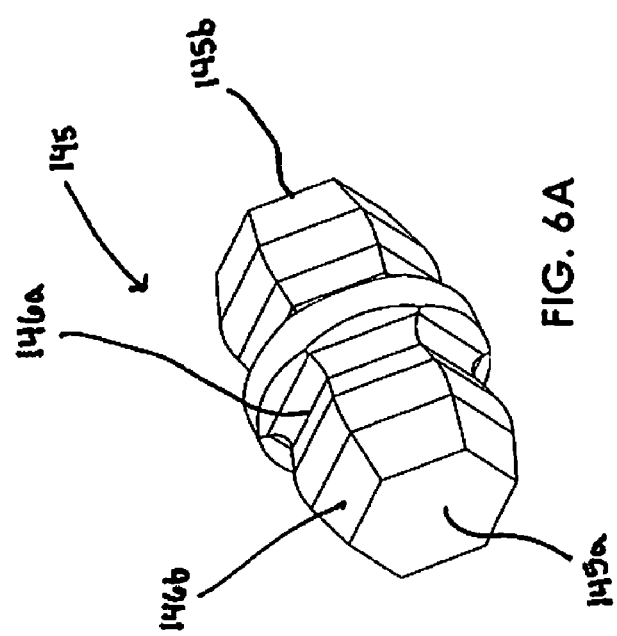

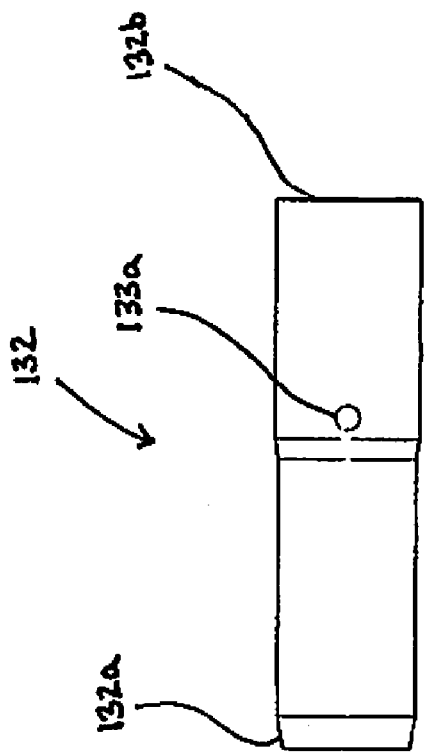
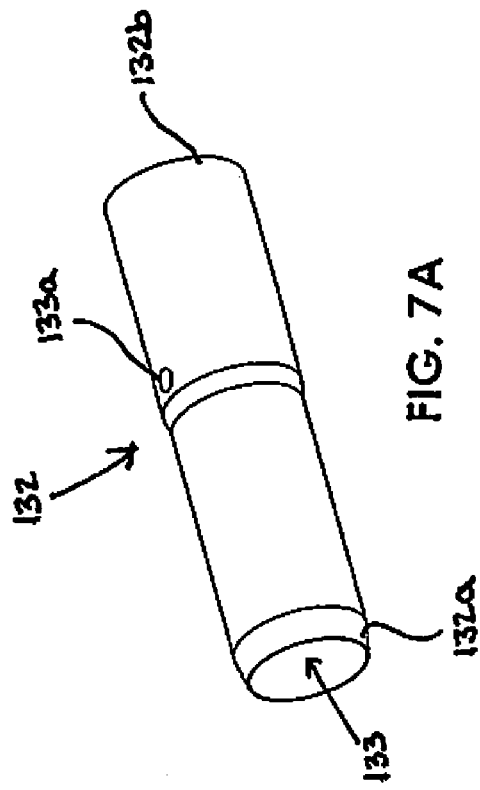

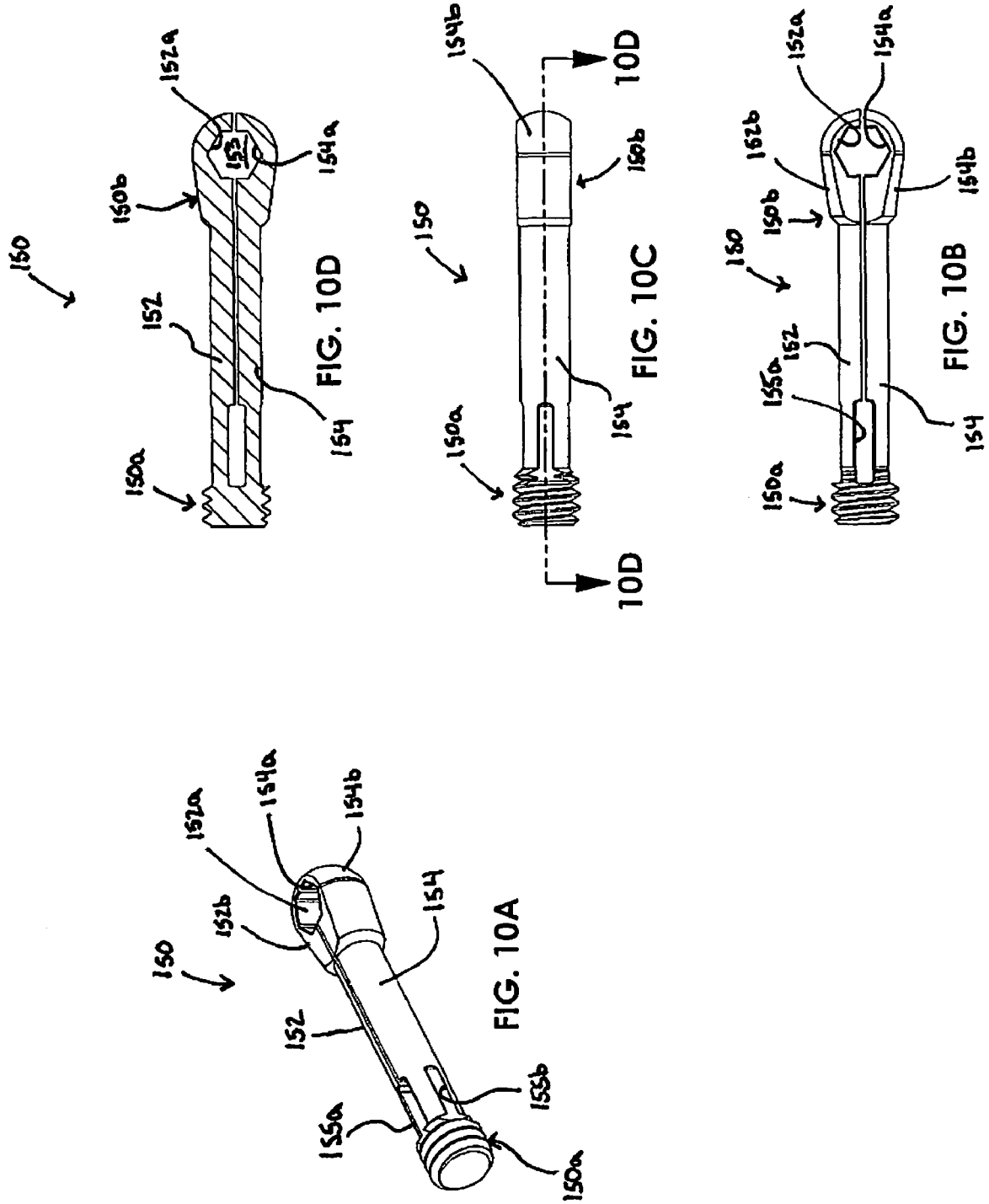

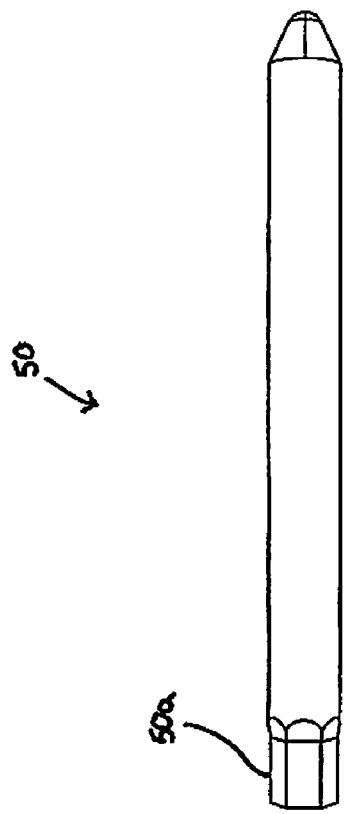
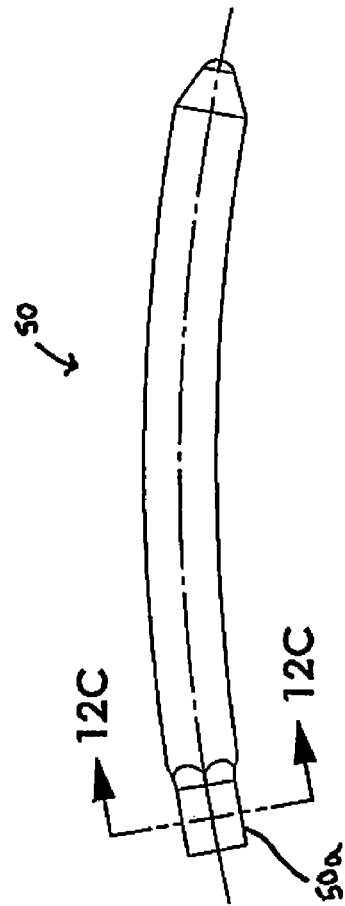
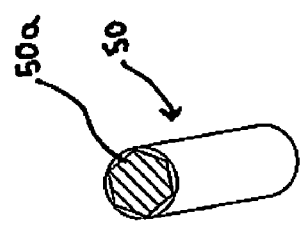
FIG. 12A
FIG. 12B
FIG. 12C

ROD INSERTION INSTRUMENT AND METHOD OF USE

CROSS-REFERENCE TO RELATED APPLICATIONS

This application claims priority to, and the benefit of, U.S. Provisional Patent Application Ser. No. 60/999,946, filed Oct. 23, 2007, the contents of which are hereby incorporated by reference in their entirety.

BACKGROUND

1. Technical Field

The present disclosure relates generally to orthopedic spinal surgery, and more particularly, to devices and methods for inserting a rod during spinal surgery.

2. Background of Related Art

The spinal column is a complex system of bones and connective tissues that provide support for the human body and protection for the spinal cord and nerves. The adult spine is comprised of twenty-four vertebral bodies, which are subdivided into three areas, including seven cervical vertebrae, twelve thoracic vertebrae and five lumbar vertebrae. Between each vertebral body is an intervertebral disc that cushions and dampens the various translational and rotational forces exerted upon the spinal column.

There are various disorders, diseases and types of injury which the spinal column may experience in a lifetime. These problems may include, but are not limited to, scoliosis, kyphosis, excessive lordosis, spondylolisthesis, slipped or ruptured discs, degenerative disc disease, vertebral body fracture, and tumors. Persons suffering from any of the above conditions typically experience extreme or debilitating pain and often times diminished nerve function.

One of the more common solutions to any of the above mentioned conditions involves a surgical procedure to implant a rod or rods along the spine to support the vertebral bodies. Typically, the implanted rod is attached to the vertebral bodies using pedicle screws, hooks or anchors. Although instruments have been designed to assist in the insertion of the rod through the implanted screws, hooks or anchors, there exists a need for an improved insertion device.

SUMMARY

Accordingly, an insertion tool for selectively receiving and manipulating a spinal rod is provided. The insertion tool includes a handle assembly, an upper body portion, an elbow portion, a lower body portion and a drive mechanism. The drive mechanism extends from the handle assembly through the upper body portion and elbow portion to operably connect to the lower body portion. The lower body portion includes a collet configured to selectively engage a spinal rod. The collect includes first and second opposed arms forming a slot in the distal end. The slot may be substantially open or substantially closed. The slot may also be hexagonal in shape.

Rotation of the handle assembly in a first direction causes the approximation of the first and second arms of the collet towards one another. Rotation of the handle assembly in the second direction causes approximation of the first and second arms of the collet away from each other. Once a spinal rod is securely attached to the lower body portion, the insertion tool may be used to manipulate a spinal rod through one or more pedicle screws.

BRIEF DESCRIPTION OF THE DRAWINGS

Embodiments of the presently disclosed insertion tool are described herein with reference to the accompanying drawings, wherein:

FIG. 1A is a top perspective view of an embodiment of the insertion tool of the present disclosure;

FIG. 1B is a cross-sectional side view of the insertion tool of FIG. 1A taken along line 1B-1B;

FIG. 1C is a bottom perspective view of the insertion tool of FIG. 1A;

FIG. 1D is an enlarged cross-sectional view of portion B of FIG. 1B;

FIG. 2A is a perspective view of an adjustment handle of the insertion tool of FIG. 1A;

FIGS. 2B and 2C are side views of the adjustment handle of FIG. 2A;

FIG. 3A is a side view of a drive shaft of the insertion tool of FIG. 1A;

FIG. 3B is a cross-sectional top view of the drive shaft of FIG. 3A taken along line 3B-3B;

FIG. 4A is a side view of an upper body portion of the insertion tool of FIG. 1A;

FIG. 4B is a cross-sectional top view of the upper body portion of the FIG. 4A;

FIG. 6A is a perspective view of a universal connector of the insertion tool of FIG. 1A;

FIG. 6B is a top view of the universal connector of FIG. 6A;

FIG. 6C is a side view of the universal connector of FIGS. 6A and 6B;

FIG. 7A is a perspective view of an insertion member of the insertion tool of FIG. 1A;

FIG. 7B is a side view of the insertion member of FIG. 7A;

FIG. 10A is a perspective view of a collet of the insertion tool of FIG. 1A;

FIG. 10B is a top view of the collet of FIG. 10A;

FIG. 10C is a side view of the collet of FIGS. 10A and 10B;

FIG. 10D is a cross-sectional top view of the collet of FIGS. 10A-10C taken along line 10D-10D of FIG. 10C;

FIG. 12A is a side view of spinal rod for use with the insertion tool of FIG. 1A;

FIG. 12 B is a top view of the spinal rod of FIG. 12A;

FIG. 12C is a cross-sectional end view of the spinal rod of FIGS. 12A and 12B taken along line 12C-12C of FIG. 12B;

DETAILED DESCRIPTION OF THE EMBODIMENTS

Figure 1E:
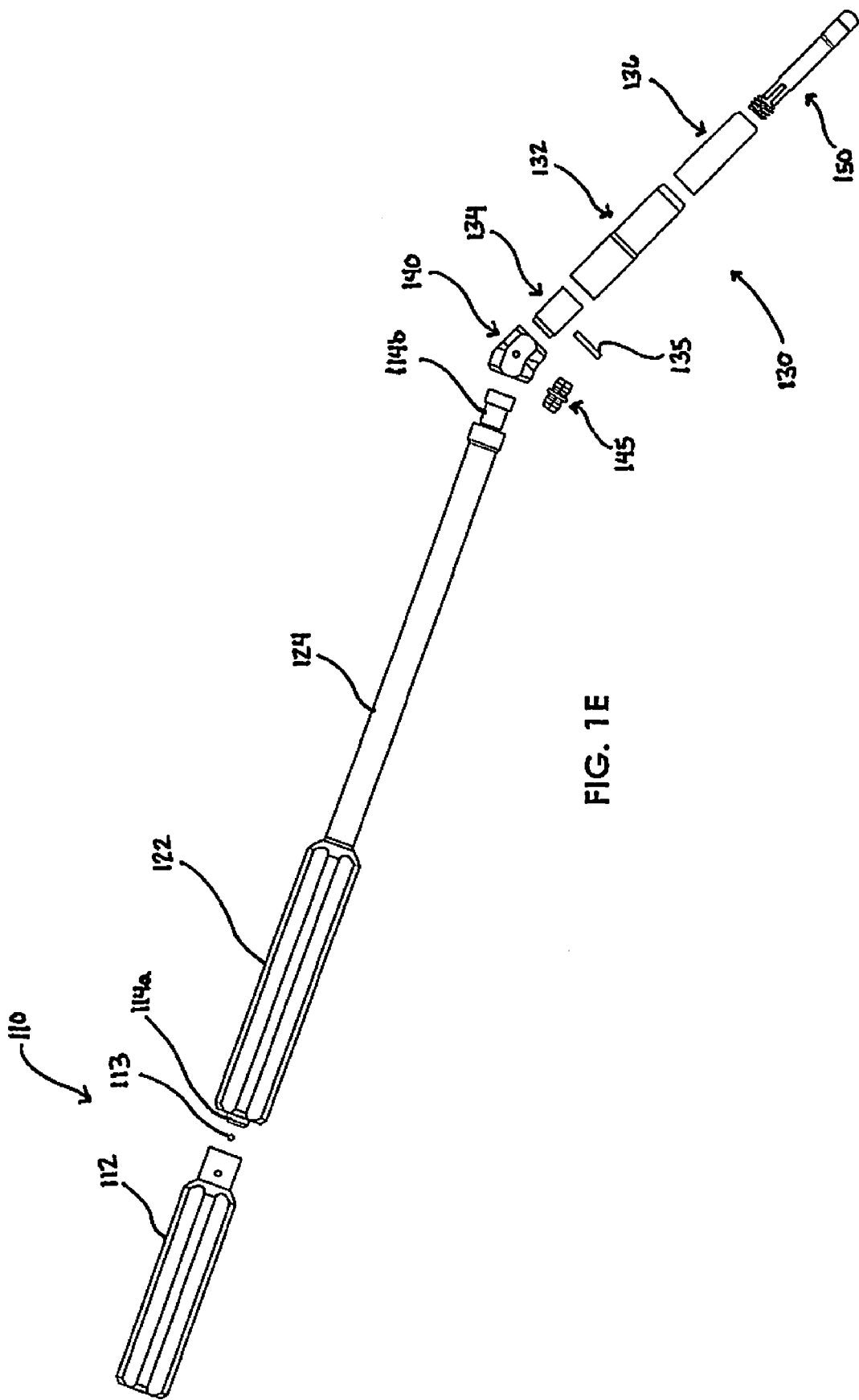
FIG. 1E is an exploded side view of the insertion tool of FIGS. 1A and 1C.

While the presently disclosed insertion tool will be described more fully hereinafter with reference to the accompanying drawings, in which particular embodiments are shown, it is to be understood at the outset that persons skilled in the art may modify the apparatus herein described while achieving the functions and results of this apparatus. Accordingly, the descriptions that follow are to be understood as illustrative and exemplary of specific structures, aspects and features within the broad scope of the present disclosure and not as limiting of such broad scope. Like numbers refer to similar features of like elements throughout.

Referring to FIGS. 1A-1E, an embodiment of the present disclosure is shown generally as insertion device 100. Insertion device 100 is configured to selectively retain and assist in insertion of a spinal rod 50 (FIGS. 12A-12C). Insertion device 100 includes a handle assembly 110, an upper body portion 120, and a lower body portion 130. Upper body portion 120 is operably connected to lower body portion 130 by an elbow member 140.

Still referring to FIG. 1B, handle assembly 110 includes an adjustment handle 112 operably connected to a drive shaft 114. Turning now to FIGS. 2A-2C, adjustment handle 112 is a substantially annular member configured for operable engagement by a user; however, it is envisioned that adjustment handle 112 may define any suitable handle configuration. Adjustment handle 112 may be composed of metal, plastic, polymer or other suitable material. Adjustment handle 112 includes a substantially open distal end 112b configured for receipt of a proximal end 114a of drive shaft 114. Distal end 112b of adjustment handle 112 further includes an opening 113 sized to receive a first connector pin 113a therein for securing drive shaft 114 with adjustment handle 112. In this manner, drive shaft 114 rotates as adjustment handle 112 is rotated. Alternatively, drive shaft 114 may be integrally formed with adjustment handle 114. As will be discussed in further detail below, rotation of adjustment handle 112 relative to upper body portion 120 causes the capture or release of the spinal rod 50 from the distal end of insertion device 100.

With reference now to FIGS. 3A and 3B, drive shaft 114 is configured to extend the length of upper body 120 (FIG. 1A). As discussed above, drive shaft 114 is securely affixed to adjustment handle 112 (FIG. 2A). Proximal end 114a of drive shaft 114 is configured for insertion into open distal end 112b of adjustment handle 112. Proximal end 114a defines an opening 115 for receiving a first connector pin 113a (FIG. 1E). A distal end 114b of drive shaft 114 is configured to engage a proximal end 145a of a universal connector 145 (FIG. 6A-6C). As will be discussed in further detail below, distal end 114b of shaft 114 defines a hexagonal cross-sectional profile configured to receive proximal end 145a of universal connector 145. It is envisioned that distal end 114b may define any shaped cross-sectional profile suitable for operable engagement with proximal end 145a of universal connector 145.

Figure 5B:
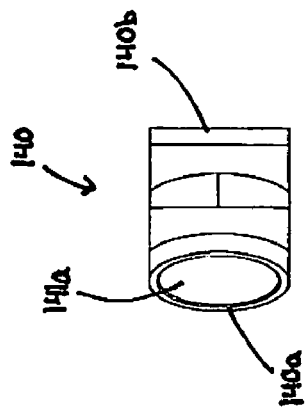
FIG. 5B is a top view of the elbow connector of FIG. 5A.
Figure 5D:
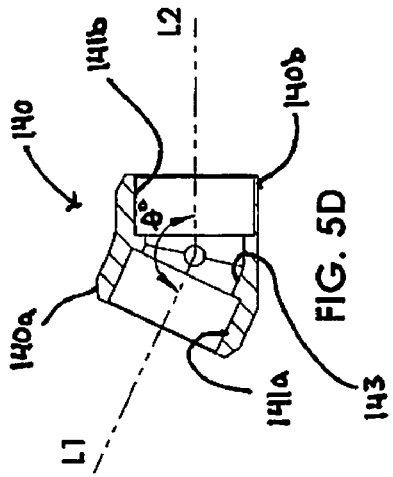
FIG. 5D is a cross-sectional top view of the elbow connector of FIG. 5A-5C taken along line 5D-5D of FIG. 5C.
Figure 5C:
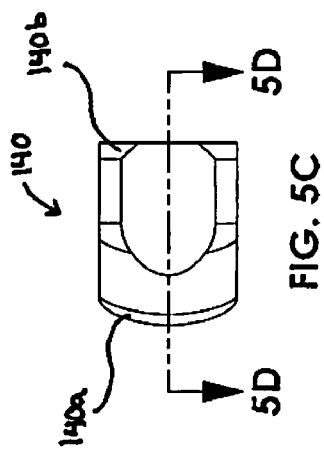
FIG. 5C is a bottom view of the elbow connector of FIGS. 5A and 5B.
Figure 5A:
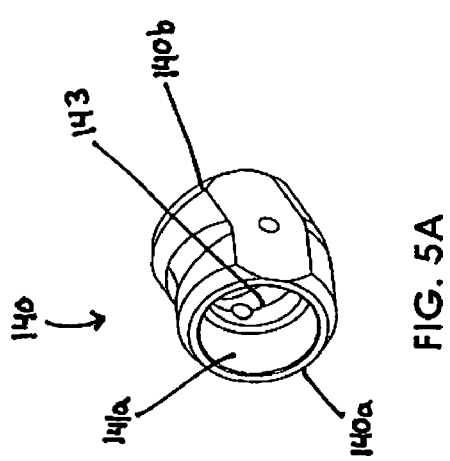
FIG. 5A is a perspective view of an elbow connector of the insertion tool of FIG. 1A.

Turning to FIGS. 4A and 4B, upper body portion 120 includes a stationary handle 122 and an elongated member 124 extending therefrom. Stationary handle 122 and elongated member 124 define a lumen 123 therethrough for receipt of drive shaft 114. Stationary handle 122 forms a substantially elongated member 124 rigidly secured with elongated member 124. Stationary handle 122 may be integrally formed with elongated member 124. Alternatively, stationary handle 122 may be formed independent of elongated member 124 and may be connected thereto using any known connection means. As will be discussed in further detail below, distal end 124b of elongated member 124 is configured for operable engagement with a proximal end 140a of elbow member 140 (FIG. 5A).

Referring to FIGS. 5A-5D, elbow member 140 includes proximal and distal ends 140a, 140b defining proximal and distal annular portions 141a, 141b, respectively. As will be discussed below, proximal and distal annular portions 141a, 141b are configured to receive proximal and distal ends 145a, 145b of universal connector 145, respectively. As discussed above, first proximal end 140a is configured for operable engagement with distal end 124b of elongated member 124. Proximal end 140a of elbow member 140 and distal end 124b of elongated member 124 may be press-fit, welded, bonded or otherwise fastened with one another. As will be discussed in greater detail below, distal end 140b of elbow member 140 is configured for operable engagement with a proximal end 132a of extension member 132. Elbow member 140 further includes a cavity 143 between proximal and distal annular portions 141a, 141b configured to retain universal connector 145. As shown, proximal and distal annular portions 141a, 141b are formed at approximately a one hundred and fifty-five degree (155°) angle θ relative to one another. It is envisioned that proximal and distal annular portions 141a, 141b may be formed at an angle θ anywhere from ninety degrees (90°) up to and including one-hundred and eight degrees (180°). It is further envisioned that elbow member 140 may include a mechanism (not shown) for adjusting angle θ between proximal and distal annular portions 141a, 141b.

With reference to FIGS. 6A-6C, universal connector 145 defines a substantially rigid member including proximal and distal ends 145a, 145b and an annular middle section 146 therebetween. Annular middle section 146 of universal connector 145 is configured to be rotatably maintained within cavity 143 formed in elbow member 140 (FIG. 5A). Proximal and distal end 145a, 145b are substantial mirror images of one another and will be described in detail as relates to proximal end 145a. Proximal end 145a of universal connector 145 defines a substantially hexagonal cross-sectional profile. Proximal end 145a further defines first and second engaging surfaces 146a, 146b. First and second engaging surface 146a, 146b are angled or curved such that when universal connector 145 is received within elbow connector 140, proximal end 145a of universal connector 145 is received within distal end 114b of drive shaft 114 (shown in phantom). This configuration permits the transfer of a rotational force from drive shaft 114 along a first longitudinal axis L1 to threaded nut 134 (FIG. 5B) along a second longitudinal axis L2.

Referring back to FIG. 1E, lower body portion 130 of insertion tool 100 includes extension member 132, a threaded nut 134, a collet ring 136 and a collet 150. Turning now to FIGS. 7A-7C, extension member 132 defines a substantially annular member including proximal and distal ends 132a, 132b. Proximal end 132a of extension member 132 is configured for operable engagement with distal end 140b of elbow connector 140. Proximal end 132a of extension member 132 may be press-fit, welded, bond or otherwise connected with distal end 140b of elbow connector. Extension member 132 defines a lumen 133 configured to receive threaded nut 134 (FIG. 8B) in a proximal end thereof and collet ring 136 (FIG. 9A), including collet 150 (FIG. 10A) inserted therethrough, in a distal end thereof. Extension member 132 further defines an opening 133a configured for receiving a second connector pin 135 (FIG. 1E).

Figure 8B:
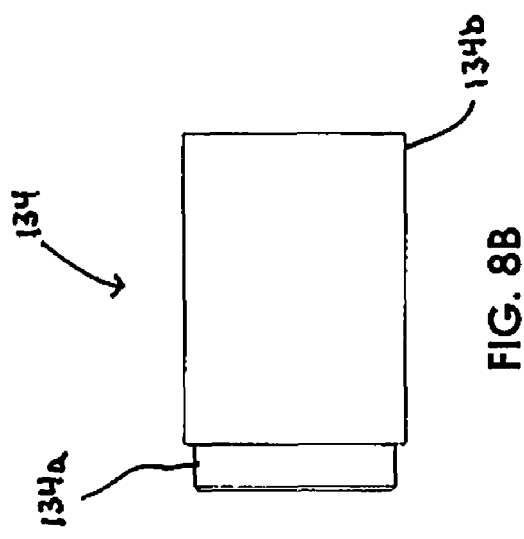
FIG. 8B is a side view of the threaded nut of FIG. 8A.
Figure 8C:
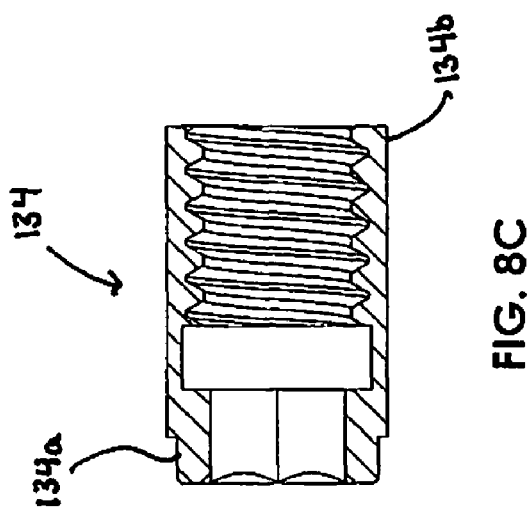
FIG. 8C is a cross-sectional side view of the threaded nut of FIGS. 8A and 8B taken along line 8C-8C of FIG. 8A.
Figure 8A:
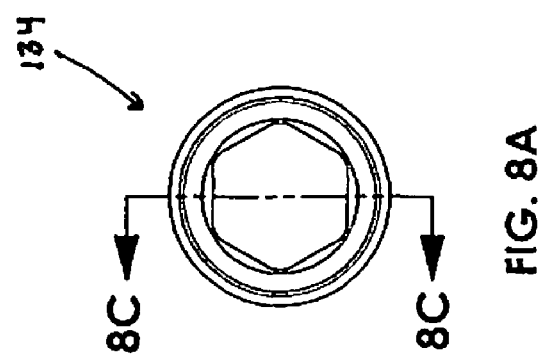
FIG. 8A is a proximal end view of a threaded nut of the insertion tool of FIG. 1A.

With reference to FIGS. 8A-8C, threaded nut 134 defines a substantially annular member including a proximal end 134a and an internally threaded distal end 134b. Proximal end 134a defines an opening having a substantially hexagonal cross-sectional profile. Proximal end 134a is configured to receive distal end 142b of universal connector 142 (FIG. 8B). As will be discussed in further detail below, threaded distal end 134b is configured to engage a threaded proximal end 150a of collet 150 (FIG. 10A).

Figure 9B:
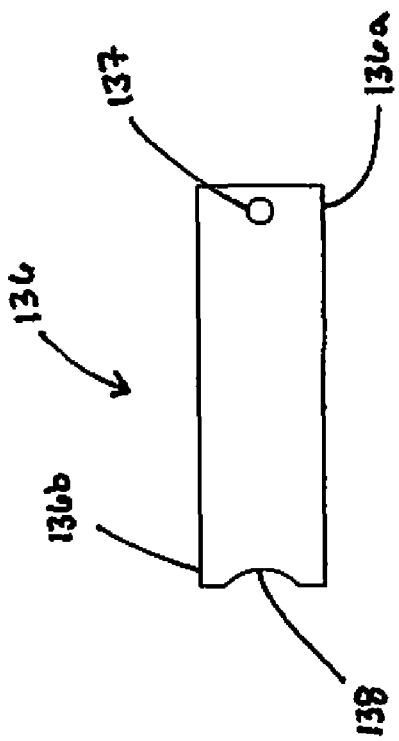
FIG. 9B is a top view of the collet ring of FIG. 9A.
Figure 9C:
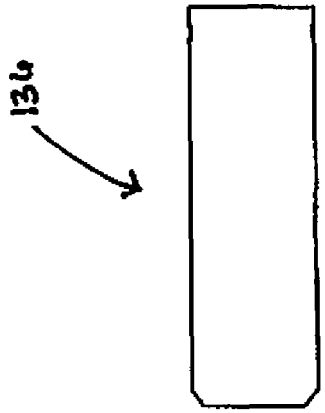
FIG. 9C is a side view of the collet ring of FIGS. 9A and 9B.
Figure 9A:
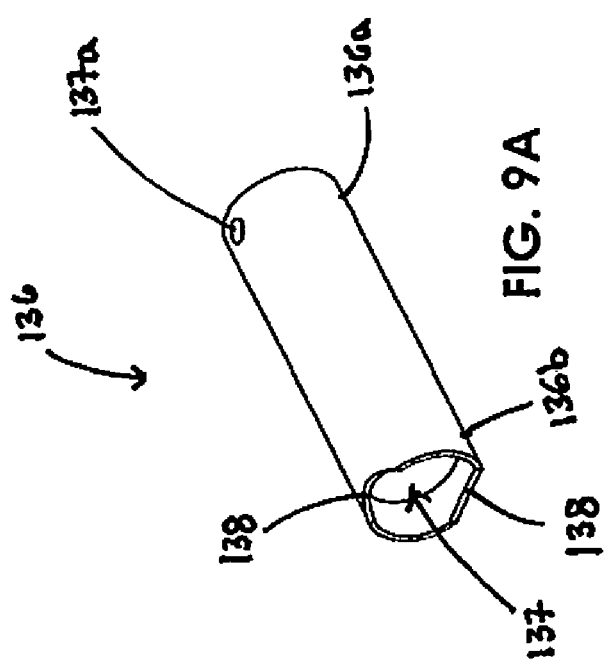
FIG. 9A is a perspective view of a collet ring of the insertion tool of FIG. 1A.

Turning to FIGS. 9A-9C, collet ring 136 defines a substantially annular member configured to be received within extension member 132. Collet ring 136 includes proximal and distal ends 136a, 136b and defines a lumen 137 therethrough. Proximal end 136a of collet ring 136 defines opening 137a for receiving second connector pin 135 (FIG. 1E). Distal end 136b of collet ring 136 may define a groove or recess 138 for accommodating a portion of a spinal rod (FIG. 11) as collet 150 (FIG. 10A) is retracted within collet ring 136.

Referring now to FIGS. 10A-10D, collet 150 includes threaded proximal end 150a and a distal end 150b configured for selectively securing a spinal rod. Distal end 150b includes a pair of substantially identical first and second arms 152, 154 extending distally from threaded proximal end 150a. First and second arms 152, 154 are spaced apart and define a channel 153 therebetween. First and second arms 152, 154 each include a rod engagement surface 152a, 154a, respectively, and a collet ring engagement surface 152b, 154b. Rod engagement surfaces 152a, 154a are configured to selectively retain proximal end 50a of spinal rod 50 (FIG. 11A) as first and second arms 152, 154 are approximated towards one another. First and second arms 152, 154 are configured such that rod engagement surfaces 152a, 154a forms a substantially closed opening 153 for receipt and selective engagement of proximal end 50a of spinal rod 50. In this manner, spinal rod 50 is top loaded into engagement with collet 150. As shown and described herein, spinal rod 50 includes proximal end 50 a having a substantial hexagonal cross-sectional profile. It is envisioned that rod engagement surfaces 152a, 154a may define an opening for receipt of a spinal rod having various cross-sectional profiles.

First and second arms 152, 154 further define a first slot 155a therebetween configured to receive second connector pin 135 (FIG. 1E) therethrough when collet 150 is in a first orientation with respect to extension member 132. First and second arms 152, 154 define a second slot 155b therethrough for receiving second connector pin 135 when collet 150 is in a second orientation relative to extension member 132. As will be discussed in further detail below, when collet 150 is in the first orientation (FIG. 1B) with respect to extension member 132, such that first slot 155a is aligned with openings 137a defined by collet ring 136 and opening 133a defined by extension member 132 to receive second connector pin 135, rod engagement surfaces 152a, 154a are positioned to retain spinal rod 50 along the longitudinal plane defined by insertion tool 100. Rotation of collet 150 ninety degrees (90°) along the longitudinal axis from the first orientation relative to extension member 132 to the second orientation relative to thereto positions rod engagement surfaces 152a, 154a to retain spinal rod 50 perpendicular to the longitudinal plane defined by insertion tool 100.

Figure 11A:
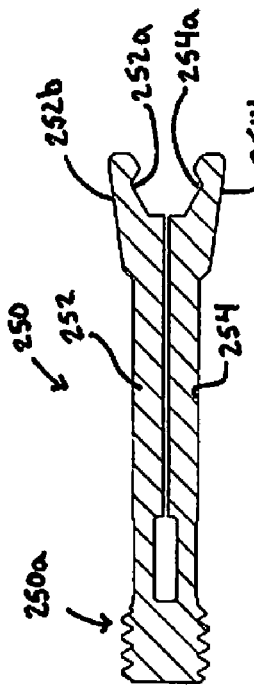
FIG. 11A is a perspective view of an alternate embodiment of collet of the insertion tool of FIG. 1A.
Figure 11B:
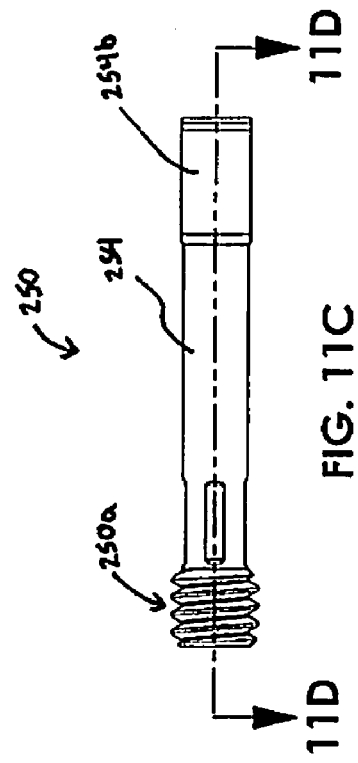
FIG. 11B is a top view of the collet of FIG. 11A.
Figure 11C:
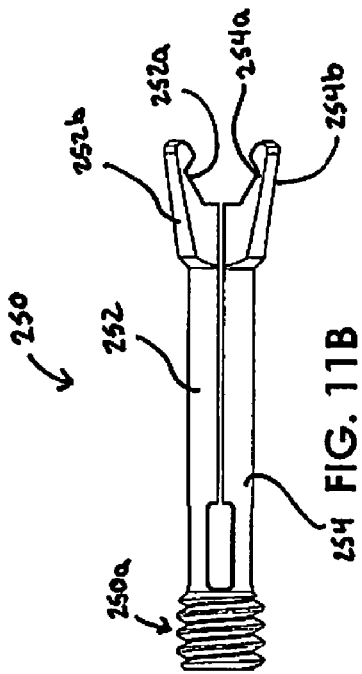
FIG. 11C is a side view of the collet of FIGS. 11A and 11B.
Figure 11D:
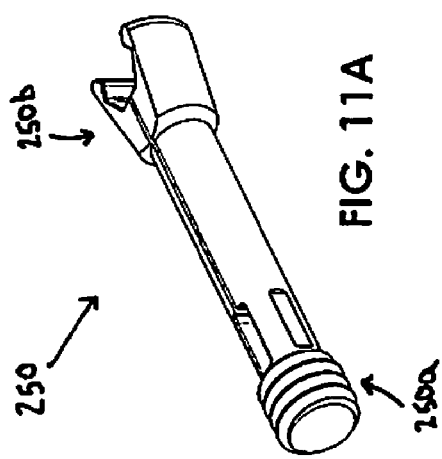
FIG. 11D is a cross-sectional top view of the collet of FIGS. 11A-11C taken along line 11D-11D of FIG. 11C.
Figures 13A, 13B:
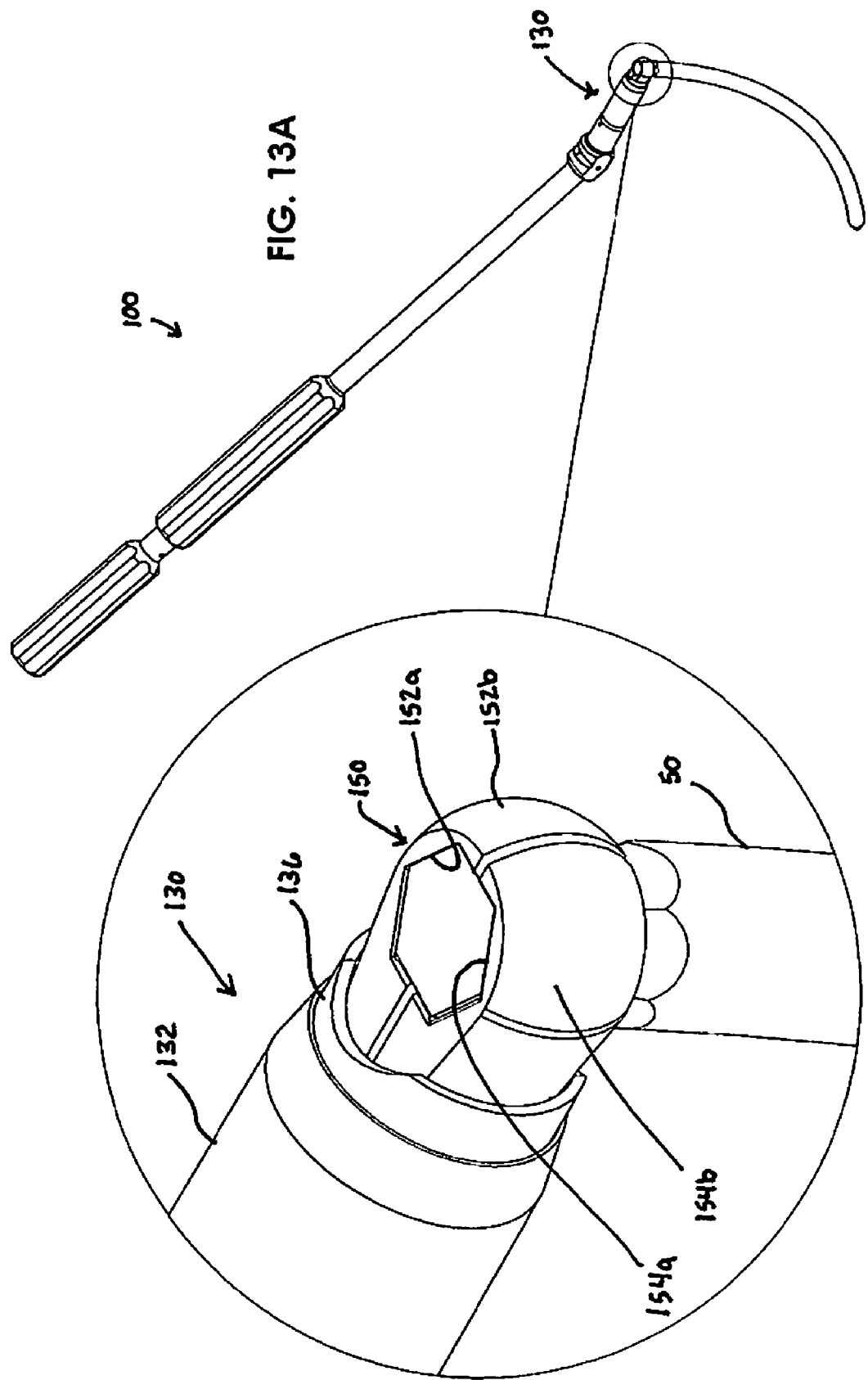
FIG. 13A is a perspective view of the insertion tool of FIG. 1A in combination with the spinal rod of FIGS. 12A and 12B.
FIG. 13B is an enlarged view of Section 13B of FIG. 13A.
Figure 14B:
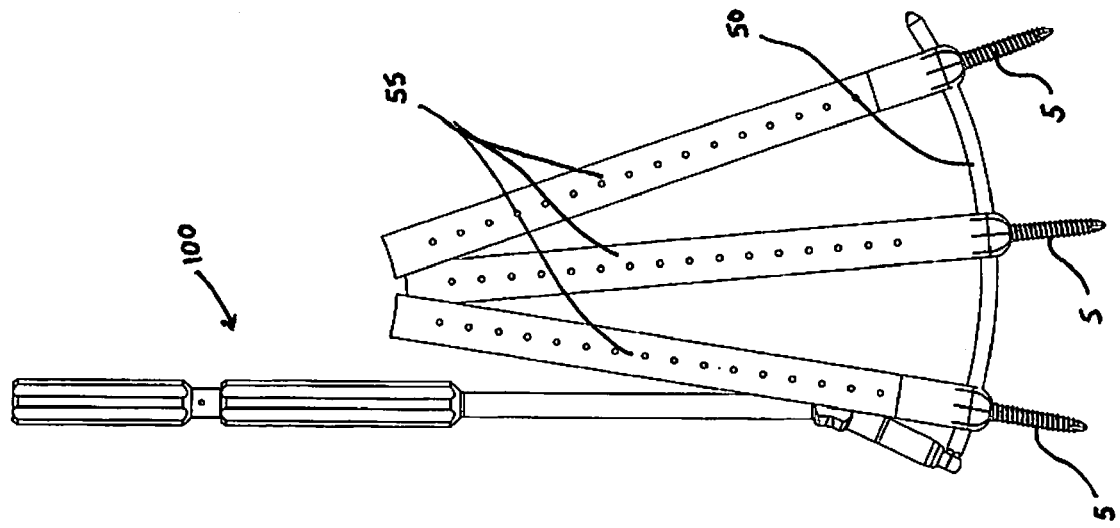
FIG. 14B is a side view of the insertion tool and spinal rod of FIG. 14A upon insertion through a series of pedicle screws.
Figure 14A:
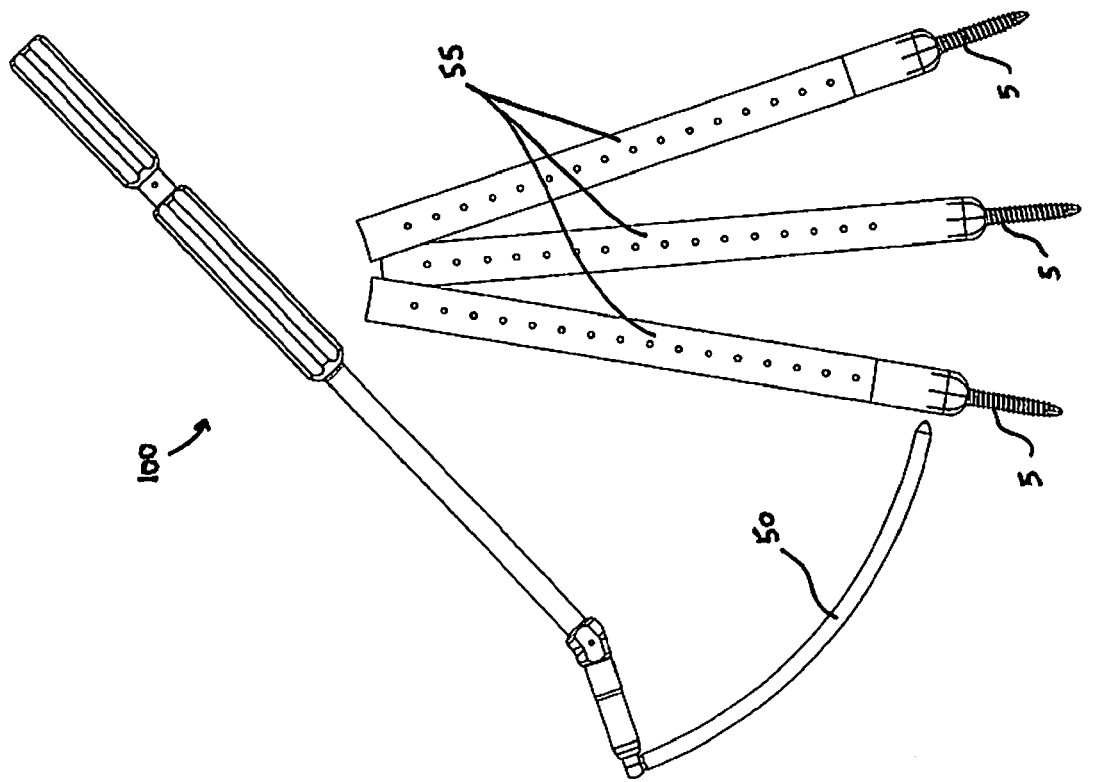
FIG. 14A is a side view of the insertion tool and spinal rod of FIG. 13A prior to insertion through a series of pedicle screws.
Figure 15:
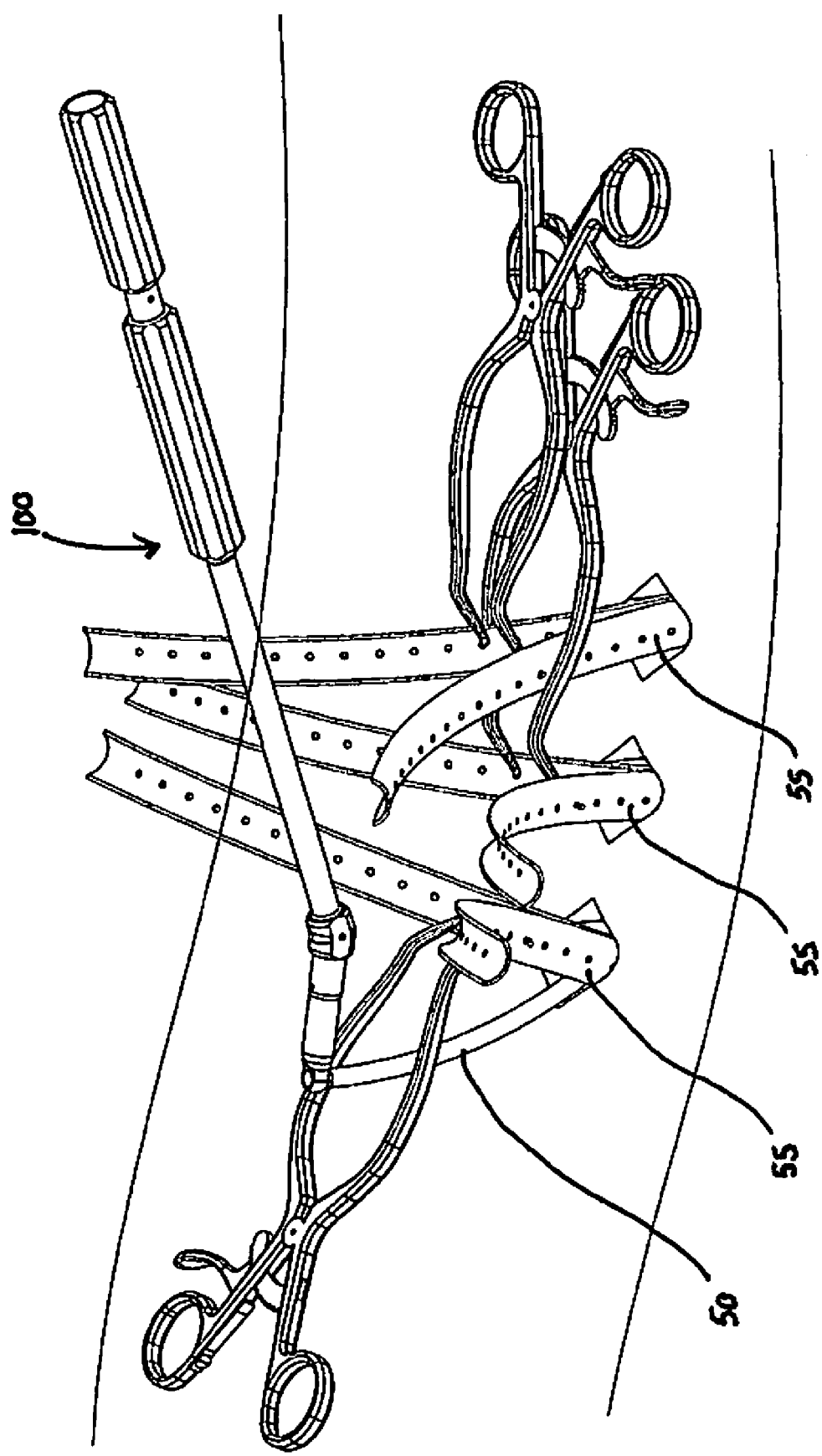
FIG. 15 is a perspective view of the insertion tool and rod of FIGS. 13A-14B during a spinal surgery procedure.
Figure 16A:
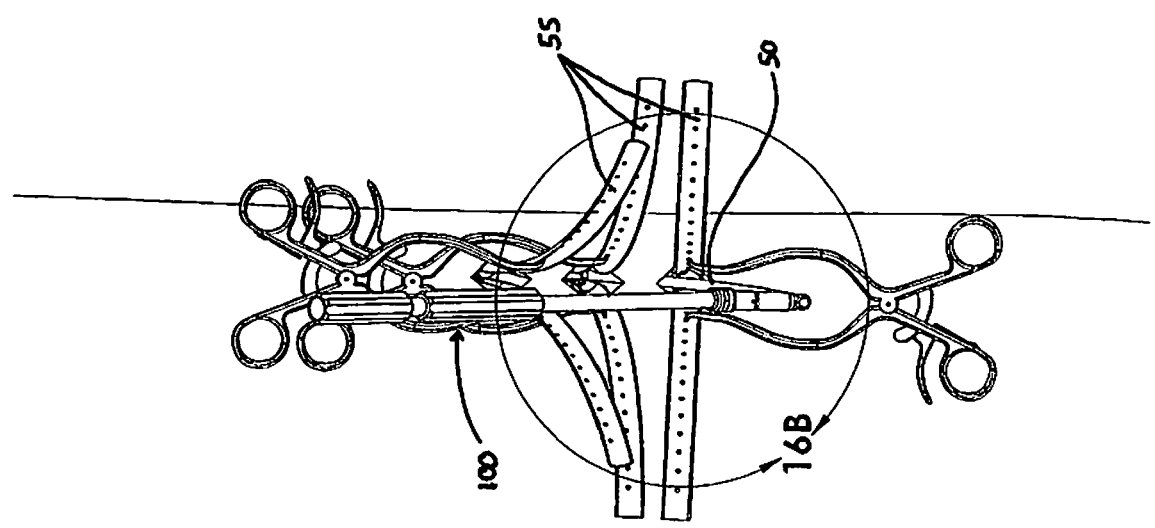
FIG. 16A is a top view of the insertion tool and rod of FIG. 15.
Figure 16B:
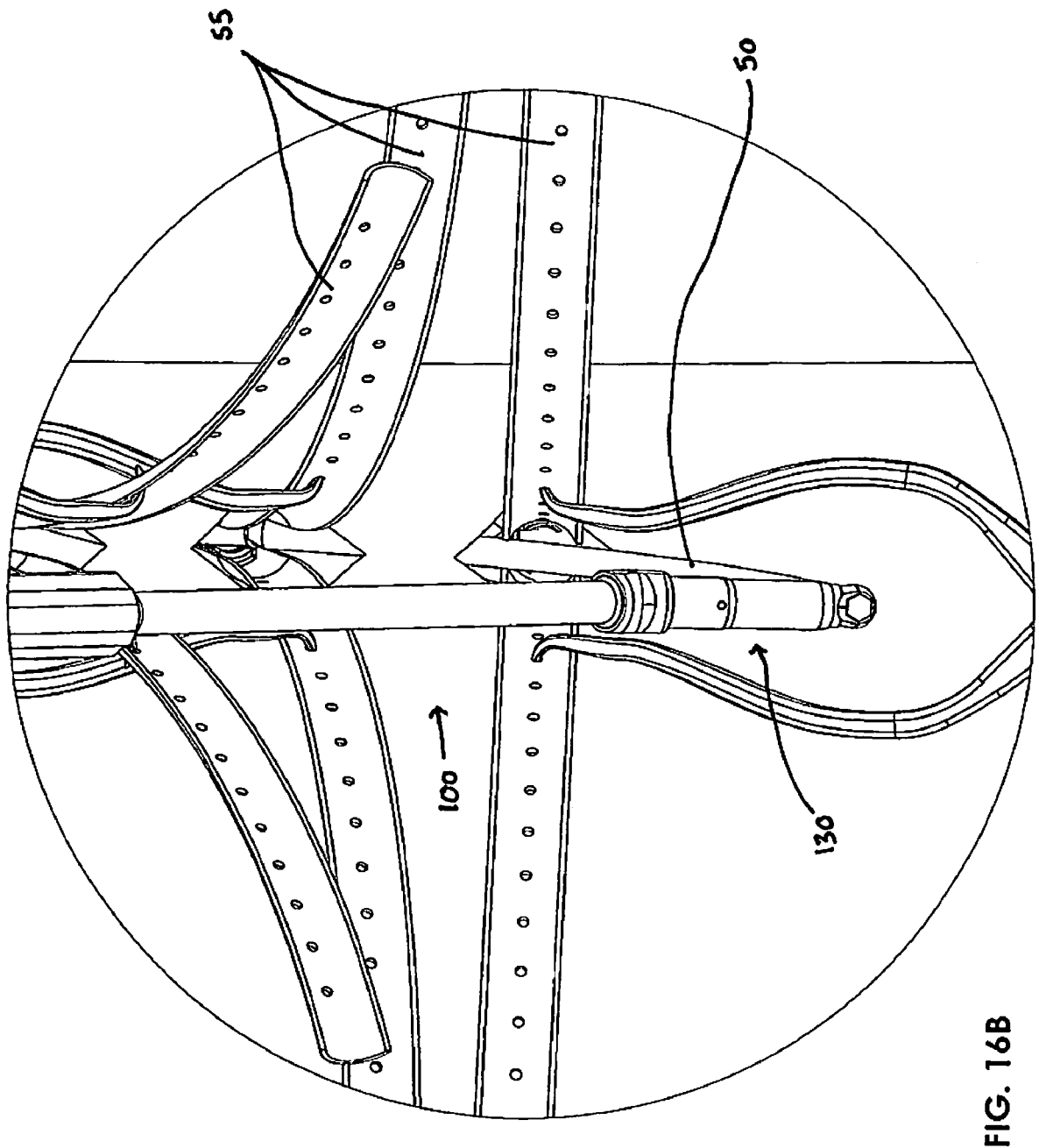
FIG. 16B is an enlarged view of Section 16B of FIG. 16A.

With reference to FIGS. 11A-11C, an alternate embodiment of a collet according to the present disclosure is shown generally as collet 250. Collet 250 is substantially similar in form and function to collect 150 described hereinabove. Collect 250 includes a threaded proximal end 250a and a distal end 250b including first and second arms 252, 254. Each of first and second arms 252, 254 include a rod engagement surface 252a, 254a, respectively. Rod engagement surfaces 252a, 254a define a substantially open opening 253 for receipt of proximal end 50a of spinal rod 50. In this manner, spinal rod 50 may be loaded into engagement with collet 50 laterally, as well as from the top.

The assembly of insertion tool 100 will now be described with reference to FIGS. 1A-1E. Initially, drive shaft 114 is affixed to adjustment handle 112 with connector pin 113a. As discussed above, drive shaft 114 may instead be integrally formed with adjustment handle 112. Distal end 114b of drive shaft 114 is received through stationary handle 122 and elongated body 124. Elbow connector 140, if not already secured to distal end 124b of elongated member 124, may then be secured to distal end 124b. Universal connector 145 is positioned within cavity 143 of elbow connector 140 such that proximal end 145a of universal connector 145 is received within distal end 114b of drive shaft 114 (see FIG. 1D). Lower body portion 130 is assembled by first inserting collet ring 136 into extension member 132. Collet 150 may then be received through collet ring 136. Depending on the desired orientation of rod engagement surfaces 152a, 154a, collet 150 is rotated until either first or second slot 155a, 155b aligns with openings 133a, 137a formed in elongated member 132 and collet ring 136, and then second connector pin 135 is inserted therethrough to maintain collet 150 within extension member 132. Threaded nut 134 may be inserted into proximal end 132a of elongated member 132, whereupon threaded distal end 134b engaged of threaded nut 134 may be engaged with threaded proximal end 150a of collet 150. Proximal end 132a of elongated member 132 may then be secured to distal end 140b of elbow member 140, with distal end 145b of universal connector 145 engaging proximal end 134a of threaded nut 134.

In operation, spinal rod 50 is initially placed between first and second rod engaging surfaces 152a, 154a. Rotation of adjustment handle 112a relative to stationary handle 122 in a first direction causes rotation of drive shaft 114 along first longitudinal axis $L_1$ (FIG. 6C). Rotation of drive shaft 114 causes the rotation of universal connector 145. Rotation of universal connector 145 causes the rotation of threaded nut 134. Rotation of threaded nut 134 causes threaded proximal end 150a of collet 150 to engage threaded distal end 134 of threaded nut 134, thereby retracting collet 150 distally relative to collet ring 136. Retraction of collet 150 causes collet ring engaging surfaces 152b, 154b thereof to engage distal end 136 of collet ring 136. Continued rotation of adjustment handle 112 in the same first direction causes the continued retraction of collet 150. As collet ring engaging surfaces 152b, 154b continue to engage distal end 136 of collet ring 136, first and second arms 152, 154 are approximated towards one another until spinal rod 50 is securely retained between first and second rod engagement surfaces 152a, 154a (FIG. 10A).

Once rod 50 is securely retained on with first and second rod engagement surfaces 152a, 154a of collet 150, insertion tool 100 may be used to manipulate rod 50 (FIGS. 13A-16B). Upon implantation of rod 50, insertion tool 100 may be disengaged from rod 50 by rotating adjustment handle 112 in an opposite second direction. In this manner, drive shaft 114 rotates universal connector 145 which in turn rotates threaded nut 134, thereby advancing collet 150 from within collet ring 136. Advancement of collet 150 relative to collet ring 136 causes collet ring engagement surfaces 152b, 154b to disengage from distal end 136b of collet ring 136. As collet ring engagement surfaces 152b, 154b disengage from collet ring 136 first and second arms 152, 154 are permitted to separate from each other thereby releasing proximal end 50a of spinal rod 50 from between first and second rod engagement surfaces 152a, 154a. Insertion tool 100 may be used repeatedly in this manner.

Advantageously, spinal rod 50 may be repositioned during insertion by loosening collet 150 around rod 50 and repositioning rod 50 to engage rod engagement surfaces 152a, 154a of collet 150 from an alternative angle to hold rod 50 in a different position relative to insertion tool 100. This repositioning feature is particularly advantageous when performing minimally invasive surgery. Referring to FIGS. 14A-16B, percutaneous retractors 55 may be used to place screws into bone (here shown as pedicle screws 5 inserted into vertebral bodies, although other applications such as trauma in long bone repair is contemplated). One suitable retractor is disclosed in U.S. patent application Ser. No. 11/528,223 filed Sep. 26, 2006, the entire content of which are hereby incorporated by reference. With the screws in place, insertion tool 100 may be used to insert rod 50 subcutaneously below the skin and fascia and to manipulate rod 50 into position relative to the screws. Spinal rod 50 is secured to the screws in the usual manner to complete the construct. The ability to adjust the relative position of the rod relative to insertion tool 100 facilitates insertion of rod 50. While the method has been described in connection with subcutaneous rod insertion, it is contemplated that the rod insert may be used in open surgery or minimally open surgery (e.g., surgery in which an incision is made between all or some of percutaneous retractors 55 shown in FIGS. 15-16B, or surgery involving a retractor for use with a less invasive technique, as shown for example in Hamada U.S. published patent application number 2007/0038216 or Jako U.S. Pat. Nos. 5,503,617 and 5,813,978.

While there has been described and illustrated specific embodiments of the rod insertion instrument apparatus, it will be apparent to those skilled in the art that variations and modifications are possible without deviating from the broad spirit and principle of the present disclosure. Therefore, this disclosure shall not be limited to the specific embodiments discussed herein.

The invention claimed is:

1. An insertion tool comprising:
   an upper body portion defining a first longitudinal axis;
   a handle assembly extending from the upper body portion;
   an elbow member connected to a distal end of the upper body portion;
   a lower body portion defining a second longitudinal axis, the lower body portion extending from the elbow and being configured to selectively engage a spinal rod, wherein the lower body portion includes an extension member, a threaded nut, a collet ring and a collet, wherein the collet ring includes a substantially annular member defining a groove in a distal end of the collet ring for accommodating a portion of a spinal rod and the collet defines a substantially hexagonal channel for receiving a hexagonal head of the spinal rod; and
   a drive mechanism extending between the handle assembly and the lower body portion for controlling the selective engagement to the spinal rod, the drive mechanism including a universal connector disposed within the elbow member and between the upper body portion and the lower body portion, the universal connector including first and second ends each having a hexagonal cross-section.

2. The insertion tool of claim 1, wherein the collet includes a pair of opposed arms configured to selectively engage a spinal rod.

3. The insertion tool of claim 2, wherein the opposed arms are approximated towards one another when the handle assembly is turned in a first direction.

4. The insertion tool of claim 3, wherein the opposed arms are approximated away from each other when the handle is turned in a second direction.

5. The insertion tool of claim 1, wherein the first longitudinal axis and second longitudinal axis are formed at an obtuse angle relative to each other.

6. The insertion tool of claim 1, wherein the first end of the universal connector is configured to rotate relative to the first longitudinal axis.

7. The insertion tool of claim 6, wherein the first end of the universal connector is configured to rotate relative to the second longitudinal axis.

8. The insertion tool of claim 1, wherein the upper portion includes a fixed handle configured to facilitate operable engagement by a user.

9. The insertion tool of claim 1, wherein the handle assembly is configured to facilitate operable engagement by a user.

10. The insertion tool of claim 1, wherein the collet forms a substantially open channel for receiving a spinal rod.

11. The insertion tool of claim 1, wherein the collet forms a substantially closed channel for receiving a spinal rod.

12. The insertion tool of claim 1, wherein the first and second ends of the universal connector are substantial mirror images of one another.

13. The insertion tool of claim 1, wherein the universal connector includes an annular section between the first and second ends.

14. The insertion tool of claim 1, wherein the collet includes a threaded proximal end configured for operable engagement with the threaded nut.

15. The insertion tool of claim 1, wherein the drive mechanism further includes a draft shaft, the drive shaft defines a recess in a distal end thereof configured to receive the first end of the universal connector.

16. The insertion tool of claim 1, wherein the threaded nut defines a recess in a proximal end thereof configured to receive the second end of the universal connector.

17. The insertion tool of claim 1, wherein the collet defines a slot in a proximal portion thereof configured to receive a connector pin for operably connecting the collet to the collet ring and the extension member.

* * * * *